US00PP16713P3

(12) United States Plant Patent

Miyazaki et al.

(10) Patent No.: US PP16,713 P3
(45) Date of Patent: Jun. 27, 2006

(54) *VIOLA* PLANT NAMED 'SUNVIOLAMARI'

(50) Latin Name: *Viola cornuta*
Varietal Denomination: Sunviolamari

(75) Inventors: Kiyoshi Miyazaki, Shiga (JP); Naoto Takamura, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 104 days.

(21) Appl. No.: 10/949,332

(22) Filed: Sep. 27, 2004

(65) Prior Publication Data

US 2006/0070153 P1 Mar. 30, 2006

(51) Int. Cl.
*A01H 5/00* (2006.01)

(52) U.S. Cl. ..... Plt./323
(58) Field of Classification Search ..... Plt./323
See application file for complete search history.

(56) References Cited

PUBLICATIONS

"Flower & Green, Autumn and Winter Catalog 2003", Published by Suntory Flowers Limited of Tokyo, Japan, Jun. 1, 2003.
"Catalog for Commercial Breeders, Autunm '97 to Spring of '98", Published by Sakata Seed Co. of Japan, 1997.
"Catalog for Commercial Producers 1997–1998", Published by Takii Seed Co. of Japan, 1997.

*Primary Examiner*—Anne Marie Grunberg
*Assistant Examiner*—June Hwu
(74) *Attorney, Agent, or Firm*—Buchanan Ingersoll PC

(57) ABSTRACT

Disclosed herein is a new and distinct variety of *Viola cornuta,* named 'Sunviolamari'. This new variety has a spreading growth habit with long prostrate stems. This *Viola* plant has many branches, and a great profusion of blooms with the entire plant remaining in bloom for a considerable period of time. It displays dense green foliage, single medium-sized violet-blue flowers having some graduation of color intensity on the long peduncles. The flowers have a faint and sweet scent. The plant exhibits good resistance to rain, cold, disease and pests.

2 Drawing Sheets

Botanical classification/commercial classification: *Viola cornuta*/Viola Plant.
Varietal denomination: cv. Sunviolamari.

BACKGROUND OF THE VARIETY

The present invention relates to a new and distinct variety of *Viola cornuta* named 'Sunviolamari' that originated from the crossing a *Viola* hybrid variety named '0V-37-1' as the female parent and a variety named '0V-72A' as the male parent.

In April 2000, crossing of '0V-37-1' as the female parent and '0V-72A' as the pollen parent was conducted as Yokaichi-shi, Shiga, Japan. In May 2000, some seeds were obtained from that crossing. In August 2000, the seeds were sown and 20 seedlings were obtained. Three of the seedlings were selected in view of their spreading growth habit, and medium-sized flowers having a violet-blue petal color. These seedings were propagated by the use of cuttings and were grown in pots, and then a plant trial was carried out beginning in October 2001, at Yokaichi-shi, Shiga, Japan. The botanical characteristics of the plants were then examined, using the similar varieties, 'Violetto Nive' and 'Alpine Summer', for comparison. As a result, one seedling was selected and it was concluded that this *Viola* plant is distinguishable from any other variety, whose existence is known to us, and is uniform and stable in its characteristics. The new variety of *Viola* plant was named 'Sunviolamari'.

The female parent '0V-37-1' (not patented in the U.S.) is a strain from our breeding lines grown at Yokaichi-shi, Shiga, Japan, having a spreading growth habit with prostrate stems. The flower size is almost the same as the 'Sunviolamari' variety, and the petals display a white color.

The pollen parent '0V-72A' (not patented in the U.S.) is a strain of our breeding lines grown at Yokaichi-shi, Shiga, Japan, having a spreading growth habit with prostrate stems. It has smaller-sized flowers than the new 'Sunviolamari' variety, and the petals have a light blue color.

In the following description, the color information is in accordance with The R.H.S. Colour Chart of The Royal Horticultural Society, London, England.

SUMMARY OF THE VARIETY

This new variety is unlike any *Viola cornuta,* commercially available as evidenced by the following unique combinations of characteristics.

1. Spreading growth habit having long prostrate stems and many branches.
2. A great profusion of blooms with the entire plant remaining in bloom for a considerable period of time.
3. Single, medium-sized violet-blue flowers having some gradation of color intensity that are borne on the long peduncles.

The new variety 'Sunviolamari' differs from the similar variety 'Violetto Nive' (not patented in the U.S.) in the following respects.

1. The leaf of 'Sunviolamari' is larger than that of 'Violet Nive'.
2. The peduncle length of 'Sunviolamari' is longer than that of 'Violetto Nive'.
3. The flower of 'Sunviolamari' is larger than that of 'Violetto Nive'.
4. The flowers of 'Sunviolamari' and 'Violetto Nive' differ in petal color. 'Sunviolamari' has violet-blue flowers having gradation of color intensity. Those of 'Violetto Nive' are white.

5. The flowering time of 'Sunviolamari' is earlier than that of 'Violetto Nive'.

The new variety 'Sunviolamari' differs from the similar variety 'Alpine Summer' (not patented in the U.S.) in the following respects.

1. The leaves of 'Sunviolamari' are larger than those of 'Alpine Summer'.
2. The peduncle length of 'Sunviolamari' is longer than that of 'Alpine Summer'.
3. The flowers of 'Sunviolamari' are larger than those of 'Alpine Summer'.
4. The flowers of 'Sunviolamari' and 'Alpine Summer' differ in petal color. 'Sunviolamari' displays violet-blue flowers having some gradation of color intensity. Those of 'Alpine Summer' are bi-colored, the upper petal is violet, and the lateral and lower petals are yellow with dark purple veins.
5. The flowering time of 'Sunviolamari' is earlier than that of 'Alpine Summer'.

The new variety of *Viola* plant 'Sunviolamari' was asexually reproduced by the use of cuttings at Yokaichi-shi, Shiga, Japan, and the homogeneity and stability thereof were confirmed.

The instant plant retains its distinctive characteristics and reproduces true to type in successive generations.

BRIEF DESCRIPTION OF THE PHOTOGRAPHS

The accompanying photographs show, as nearly true as it is reasonably possible to make the same in color illustrations of this character, typical specimens of the new cultivar. The plants had been reproduced by the use of cuttings and were photographed during May 2002 while growing outdoors in 24 cm pots at an age of approximately 7 months at Yokaichi-shi, Shiga, Japan.

DESCRIPTION OF THE NEW VARIETY

Figure 1:
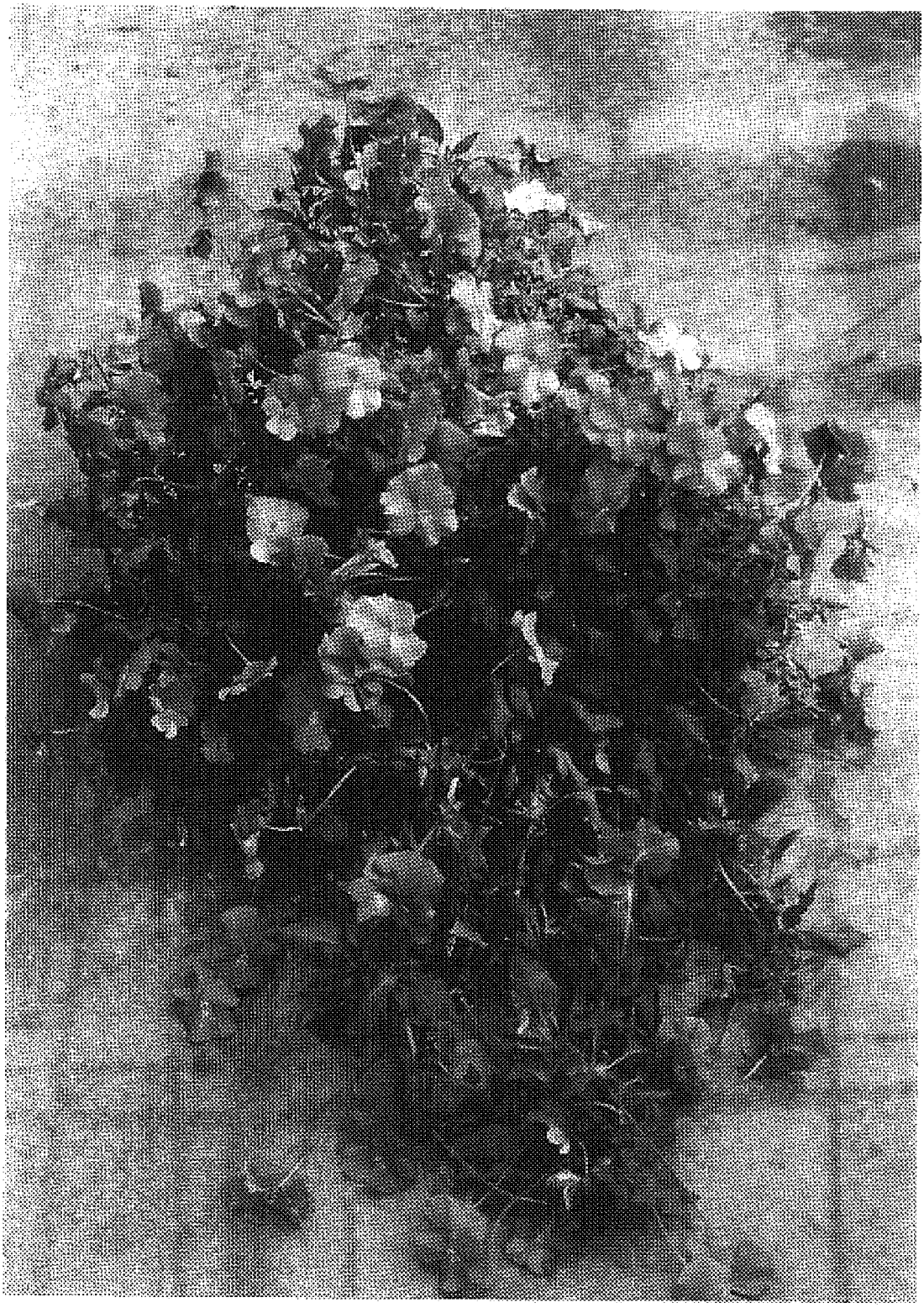
FIG. 1 illustrates an entire flowering plant of the new variety while growing in a pot.
Figure 2:
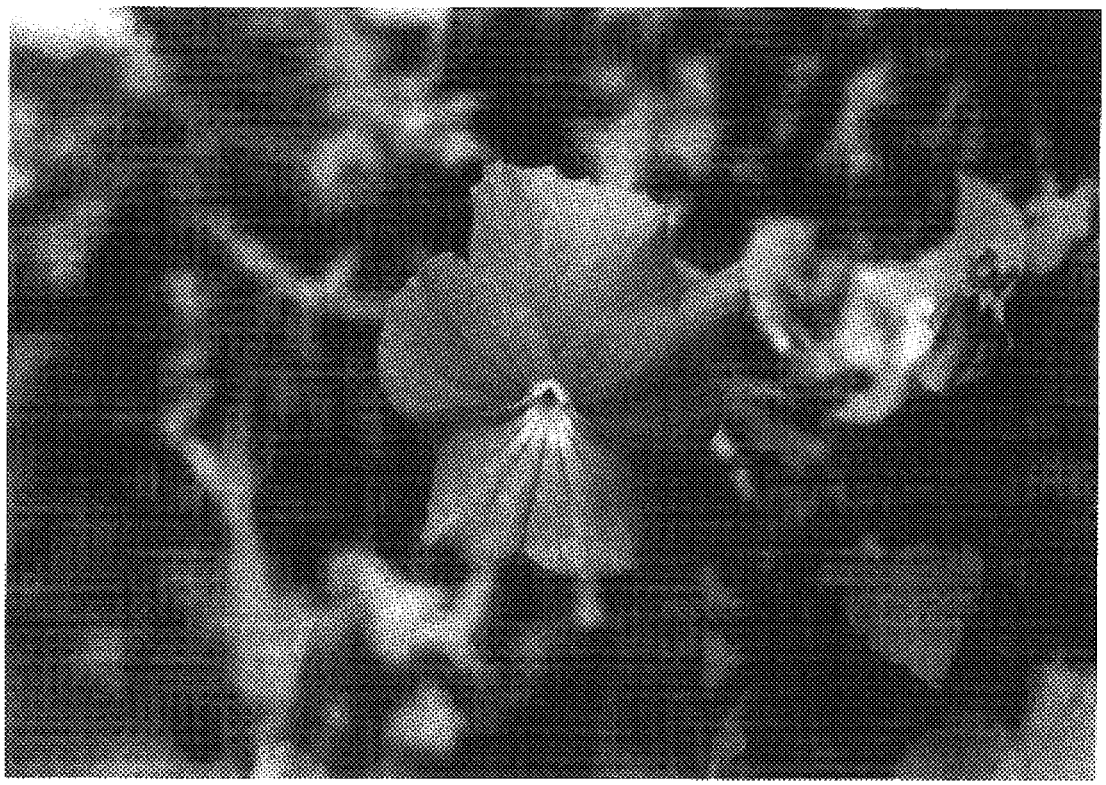
FIG. 2 illustrates a close view of the blossoms of the new variety.

The botanical characteristics of the new and distinct variety of *Viola cornuta* named 'Sunviolamari' are set forth hereafter. The plants were observed during May 2002 at Yokaichi-shi, Shiga, Japan, at an age of approximately 7 months.

Plant:

*Stemmed or stemless.*—Stemmed.
*Growth habit.*—Spreading.
*Height.*—Approximately 8 cm.
*Spreading area.*—Approximately 52 cm.

Stem:

*Length.*—Approximately 62 cm.
*Color.*—R.H.S. 144B (Yellow-Green group).
*Branches.*—Many.
*Pubescence.*—Present.
*Internode length.*—Approximately 1.5 cm.

Leaf:

*Phyllotaxis.*—Alternate
*Overall shape.*—Lanceolate.
*Apex shape.*—Acute.
*Base shape.*—Acute.
*Margin.*—Crenate.
*Length.*—Approximately 4.5 cm.
*Width.*—Approximately 3.0 cm.
*Color of upper surface.*—R.H.S. 137A (Green group).
*Color of under surface.*—R.H.S. 137C (Green group).
*Leaf texture.*—Matte and smooth.
*Venation.*—Reticulate venation, not apparent except center venation.
*Petiole length.*—Approximately 3.5 cm.
*Petiole diameter.*—Approximately 0.8 mm.
*Petiole color.*—R.H.S. 144C (Yellow-Green group).
*Stipule.*—Approximately 2.5 cm in length, 2.5 cm in width. Pinnately parted. Shape is narrowly ovate. Color of upper surface is R.H.S. 137A (Green group). Color of under surface is R.H.S. 137C (Green group).

Flower:

*Inflorescence.*—Flower solitary, axillary.
*Flower form.*—Single, 5 petals, 2 upper petals, 2 lateral petals, and a spurred lower petal.
*Longitudinal diameter.*—Approximately 6.0 cm.
*Horizontal diameter.*—Approximately 5.5 cm.
*Flower depth.*—Approximately 0.9 cm.
*Petal margin.*—Entire, weakly ruffled.
*Flower color when opening.*—Primarily violet-blue with some gradation of color intensity. Upper petal: R.H.S. 90D (Violet-Blue group). Lateral petal: R.H.S. 92D (Violet-Blue group) with darker stripes of R.H.S. 83A (Violet group) and pubescence near the throat, together with R.H.S. 155C (White group). Lower petal: R.H.S. 92D (Violet-Blue group) with darker stripes of R.H.S. 83A (Violet group) and R.H.S. 155C (White group) surrounding the eye.
*Flower color when fully open.*—Upper petal: R.H.S. 90D (Violet-Blue group). Lateral petal: R.H.S. 90D (Violet-Blue group) with darker stripes of R.H.S. 83A (Violet group) and pubescence near the throat together with R.H.S. 155C (White group). Lower petal: R.H.S. 92A (Violet-Blue group) with darker stripes of R.H.S. 83A (Violet group) and R.H.S. 155C (White group) surrounding the eye.
*Petal size.*—(Length×width) Upper petal: Approximately 3.4 cm×2.9 cm. Lateral petal: Approximately 2.0 cm×1.3 cm. Lower petal: Approximately 3.0 cm×2.0 cm.
*Petal shape.*—Upper petal: Ovate. Lateral petal: Ovate. Lower petal: Cordate, spurred.
*Eye color.*—R.H.S.17A (Yellow-orange group) on the lower petal.
*Eye size.*—Length: Approximately 3.0 mm. Width: Approximately 4.0 mm.
*Spur length.*—Approximately 8.0 mm.
*Spur diameter.*—Approximately 2.3 mm.
*Spur color.*—R.H.S.94B (Violet-blue group).
*Sepal.*—5 sepals, unequal, approximately 0.6 cm–1.6 cm, R.H.S. 144A (Yellow-green group) in coloration on both surfaces, and possess some short appendages.
*Number of flowers.*—November to March: Approximately 10 flowers per plant. March to June: Approximately 40–50 flowers per plant.
*Peduncle length.*—Approximately 14 cm.
*Peduncle thickness.*—Approximately 1.3 mm.
*Peduncle color.*—R.H.S.137C (Green group).

Reproductive organs:

*Stamen.*—Five stamens joined around the ovary. Two lower stamens commonly are spurred.

*Stamen length.*—Approximately 4.0 mm.
*Anther color.*—R.H.S. 11D (Yellow group). Tip: R.H.S. 170B (Greyed-Orange group).
*Pollen color.*—R.H.S. 11D (Yellow group).
*Pistil length.*—Approximately 6.0 mm.
*Stigma shape.*—Ellipsoidal.
*Stigma length.*—Approximately 1.5 mm.
*Stigma color.*—R.H.S. 154B (Yellow-Green group).
*Style length.*—Approximately 1.0 mm.
*Style color.*—R.H.S. 154C (Yellow-Green group).
*Ovary color.*—R.H.S. 144D (Yellow-Green group).

Seeds:

*Seed.*—Some seed development has been observed.
*Seeds color.*—R.H.S. 165A (Greyed-Orange group).
*Size.*—Approximately 2.0 mm in length, and approximately 1.0 mm in width.

Physical characteristics:

*Blooming period.*—Early November to June in Japan, except Hokkaido. A bloom commonly lasts 5–7 days on the plant.
*Fragrance.*—Faint.
*Rain tolerance.*—Strong.

This variety has survived temperatures of at least as low as −7° C.

The plant grows well at temperatures up to 25° C.

The lower and upper temperatures for plant survival have not been evaluated in detail.

No serious damage by white flies, aphids, and fungal and bacterial diseases has been observed.

This new variety of *Viola cornuta* plant 'Sunviolamari' is most suitable for potting, and growing in hanging baskets and flower beds.

It is claimed:

1. A new and distinct variety of *Viola cornuta* plant named 'Sunviolamari', substantially as herein illustrated and described.

* * * * *